United States Patent
Lerebour et al.

(10) Patent No.: US 10,231,921 B2
(45) Date of Patent: *Mar. 19, 2019

(54) USE OF AN ESSENTIAL OIL OF ORIGANUM MAJORANA, AS AN AGENT FOR TREATING AND/OR PREVENTING GREASY SKIN AND/OR THE ASSOCIATED AESTHETIC SKIN DEFECTS

(71) Applicant: L'OREAL, Paris (FR)

(72) Inventors: Géraldine Lerebour, Les Loges (FR); Pierre Lartaud, Eurre (FR); Agnes Pegeon, Meudon (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/785,970

(22) PCT Filed: Apr. 18, 2014

(86) PCT No.: PCT/EP2014/058018
§ 371 (c)(1),
(2) Date: Oct. 21, 2015

(87) PCT Pub. No.: WO2014/173846
PCT Pub. Date: Oct. 30, 2014

(65) Prior Publication Data
US 2016/0106660 A1    Apr. 21, 2016

(30) Foreign Application Priority Data

Apr. 25, 2013  (FR) ...................... 13 53781

(51) Int. Cl.
| | | |
|---|---|---|
| *A61K 8/31* | (2006.01) | |
| *A61K 8/34* | (2006.01) | |
| *A61K 8/92* | (2006.01) | |
| *A61Q 19/00* | (2006.01) | |

(52) U.S. Cl.
CPC ............... *A61K 8/922* (2013.01); *A61K 8/31* (2013.01); *A61K 8/34* (2013.01); *A61K 8/347* (2013.01); *A61Q 19/008* (2013.01)

(58) Field of Classification Search
CPC . A61K 8/922; A61K 8/31; A61K 8/34; A61K 8/347; A61Q 19/008
See application file for complete search history.

(56) References Cited

U.S. PATENT DOCUMENTS

2004/0009241 A1* 1/2004 Inomata ............... A61K 8/0212
424/725

FOREIGN PATENT DOCUMENTS

| DE | 202005019455 U1 | | 2/2006 | |
|---|---|---|---|---|
| FR | 2962333 | * | 12/2010 | ............. A61K 31/12 |
| FR | 2962333 A1 | | 1/2012 | |
| WO | WO2012002724 | * | 1/2012 | ............... A61K 8/97 |

OTHER PUBLICATIONS

Lerebour (FR 2962333; machine translation; Dec. 2010).*
Yoon (WO 2012/002724; machine translation; Jan. 2012).*
Novak et al. (J. Essential Oil Research, v. 22 (2010), p. 412-415).*
Deans et al. (Flavour and Fragrance J., vol. 5, p. 187-190 (1990).*
Tabanca et al. (J. Essent. Oil Res., 16, p. 248-252 (May-Jun. 2004).*
Guangwu et al., "Essential Oil of Origanum Majorana", Thinks About Essential Oils, Jan. 31, 2010, p. 101-102, Anhui.
Arnold et al., "Comparative Study of the Essential Oils From Three Species of Origanum Growing Wild in the Eastern Mediterranean Region", Journal of Essential Oil Research, vol. 5, Jan./Feb. 1993, pp. 71-77.
English translation of Chinese Office Action dated Feb. 24, 2017 in CN Appln No. 201480023133.9.

* cited by examiner

*Primary Examiner* — Robert H Havlin
(74) *Attorney, Agent, or Firm* — Polsinelli PC

(57) ABSTRACT

The present invention relates to the cosmetic use, as an agent for treating greasy skin and/or preventing greasy or greasy-prone skin and/or the associated aesthetic skin defects, of an essential oil of *Origanum majorana* and/or of *origanum* hybrids. The invention also relates to a cosmetic composition comprising same, to a non-therapeutic cosmetic care and/or cleansing treatment process for greasy skin, and also to said essential oil as a dermatological agent.

10 Claims, No Drawings

USE OF AN ESSENTIAL OIL OF ORIGANUM MAJORANA, AS AN AGENT FOR TREATING AND/OR PREVENTING GREASY SKIN AND/OR THE ASSOCIATED AESTHETIC SKIN DEFECTS

CROSS REFERENCE TO RELATED APPLICATIONS

This application is a National Phase filing under 35 U.S.C. § 371 of PCT/EP2014/058018 filed on Apr. 18, 2014; and this application claims priority to application Ser. No. 1353781 filed in France on Apr. 25, 2013, under 35 U.S.C. § 119. The entire contents of each application are hereby incorporated by reference.

The present invention relates to the cosmetic use of an essential oil of *Origanum majorana* and/or of *origanum* hybrids, or of a cosmetic composition comprising same, as an agent for treating and/or preventing greasy or greasy-prone skin and/or the associated aesthetic skin defects.

The invention also relates to a cosmetic treatment process intended for treating and/or preventing greasy or greasy-prone skin and/or the associated aesthetic skin defects, in particular associated with the development of *Propionibacterium acnes* microorganisms, using a composition comprising said essential oil, or a cosmetic composition comprising said essential oil.

Sebum normally constitutes a moisturizing agent for the epidermis and can be involved in the homoeostasis of the epidermis, and in particular in the proliferation and/or differentiation of epidermal cells.

It is the natural product of the sebaceous gland, which constitutes an annex of the pilosebaceous unit. It is essentially a more or less complex mixture of lipids. Conventionally, the sebaceous gland produces squalene, triglycerides, aliphatic waxes, cholesterol waxes and, possibly, free cholesterol (Stewart, M. E., Semin. Dermatol. 11, 100-105 (1992)). The action of bacterial lipases converts a variable proportion of the triglycerides formed into free fatty acids.

The sebocyte constitutes the competent cell of the sebaceous gland. The production of sebum is associated with a programme of terminal differentiation of this cell. During this differentiation, the metabolic activity of the sebocyte is essentially directed towards the biosynthesis of lipids (lipogenesis) and more precisely towards fatty acid neosynthesis.

Greasy or hyperseborrhoeic skin is characterized in particular by an excessive secretion and excretion of sebum. Conventionally, a sebum level greater than 200 µg/cm$^2$ measured on the forehead is considered to be characteristic of such greasy skin. Such skin is often associated with dilated pores. The appearance and/or the visibility of the pores is also a characteristic of greasy skin. The shininess of the skin is also associated with dilation of the pores, hence the interest in finding active agents for reducing the size of dilated pores, a manifestation perceived as being skin imperfections or aesthetic defects.

Such skin is also often associated with a thick skin grain, a modification of the surface of the skin which may be subsequent to a desquamation defect, such as a state of roughness of the skin, or an uneven relief, manifestations perceived as being skin imperfections or aesthetic defects, hence the interest in finding active agents which limit or reduce the cohesion of the stratum corneum and which exhibit a desquamating effect. Indeed, the upper layer of the epidermis, called horny layer (or stratum corneum, SC), consists of a collection of layers of keratinocytes at the terminal stage of their differentiation, called corneocytes.

The stacking of the corneocytes constitutes the horny layer which is responsible for the barrier function of the epidermis. In the course of the normal desquamation process, the most superficial corneocytes detach from the surface of the epidermis. In a certain number of situations, it may be desired to stimulate this desquamation mechanism or process in order to promote epidermal renewal and restore or reinforce a healthy physiological state of the skin. In particular, it is possible to take advantage of the stimulation of the skin desquamation mechanism in order to, inter alia, to reduce the surface irregularities and to smooth the skin.

Moreover, such greasy or greasy-prone skin, and the aesthetic defects or skin imperfections thereof, may be associated, in addition to excess sebum, with the development of *Propionibacterium acnes* microorganisms. The microorganism *Propionibacterium acnes* (*P. acnes*) belongs to the Gram-positive anaerobic bacteria which prefer to grow in oxygen-deprived environments, such as at the bottom of a hair follicle or of an obstructed sebaceous duct. More specifically, the bacteria present in a hair follicle use sebum as a source of energy and release certain enzymes, such as lipases which convert sebum triglycerides into irritant and comedogenic fatty acids, and proteases which are responsible for rupturing the comedone sac. An inflammatory reaction may then occur, followed by the formation of undesirable spots. This microorganism thus develops more particularly in individuals with a greasy skin.

To combat hyperseborrhoea, various compounds have already been proposed, which, by topical application to the skin, are capable of reducing the lipogenesis of the sebocytes and consequently of limiting the production of sebum. The treatments currently available with regard to hyperseborrhoea are not completely satisfactory, in particular from the viewpoint of the side effects which are frequently associated therewith, such as irritative side effects with certain topical agents, for instance retinoids and benzoyl peroxides.

There remains therefore a need to have novel active agents capable of exerting a beneficial cosmetic action on greasy or greasy-prone skin and/or the associated aesthetic defects, in particular a cosmetic or dermatological action beneficial on the skin imperfections associated with the development of *Propionibacterium acnes* microorganisms.

The applicant has discovered, surprisingly and unexpectedly, that the use of a particular essential oil of *Origanum majorana* and/or of *origanum* hybrids could prove to be of use for effectively preventing and/or treating greasy or greasy-prone skin and/or aesthetic skin defects associated, in particular, with the skin imperfections associated with the development of *Propionibacterium acnes* microorganisms or associated with a desquamation defect.

A subject of the present invention is therefore the cosmetic use of at least one essential oil of *Origanum majorana* and/or of *origanum* hybrids, comprising more than 18% by weight of cis-4-thujanol and more than 16% by weight of carvacrol relative to the total weight of the constituents of the essential oil, in particular an essential oil of *Origanum majorana* L., in particular of *Origanum majorana* L. CT thujanol or of *Origanum* X *majoricum Cambassedes,* or of a cosmetic composition comprising same, as an agent for treating and/or preventing greasy or greasy-prone skin and/or the associated aesthetic skin defects.

More particularly, a subject of the invention is the cosmetic use of at least one essential oil of *Origanum majorana* and/or of *origanum* hybrids, comprising more than 18% by weight of cis-4-thujanol and more than 18% by weight of carvacrol relative to the total weight of the constituents of the essential oil, in particular an essential oil of *Origanum* majorana L., in particular of *Origanum majorana* L. CT thujanol or of *Origanum X majoricum Cambassedes,* or of a cosmetic composition comprising same, as an agent for treating and/or preventing greasy or greasy-prone skin and/or the associated aesthetic skin defects.

The term "skin" is intended to mean all of the skin of the body, and the scalp, and preferably the skin of the face, neckline, neck, arms and forearms, or even more preferably still the skin of the face (in particular of the forehead, nose, cheeks and chin), neckline and neck.

The term "care" is intended to mean a non-therapeutic care capable of producing an aesthetic effect without, however, preventing or correcting a pathological dysfunction of the skin of the body.

According to the invention, the term "preventing" or "prevention" is intended to mean reducing the probability of occurrence or reducing a risk of manifestation of the phenomenon concerned.

According to one embodiment, an associated aesthetic skin defect may be chosen from skin imperfections due to hyperseborrhoea and/or due to a desquamation defect. According to another embodiment of the invention, the aesthetic skin defects or skin imperfections are associated with the development of *Propionibacterium acnes* microorganisms.

Preferably, the signs of the associated aesthetic skin defects according to the invention are skin imperfections chosen from skin in which the follicular orifices and/or the pores are dilated, skin in which the follicular orifices and/or the pores are filled with horny spicules or comedones, and/or blackheads, a state of roughness of the skin (or rough skin), a thick skin grain, and/or skin exhibiting an uneven relief.

The signs of the associated aesthetic skin defects more particularly considered by the invention may be skin in which the follicular orifices and/or the pores are dilated, skin in which the follicular orifices and/or the pores are filled with horny spicules or comedones, and/or blackheads.

The aesthetic skin signs more particularly considered by the invention may be skin imperfections which are a modification of the skin surface associated with a desquamation defect, and are chosen from a state of roughness of the skin (or rough skin), a thick skin grain, and/or an unevenness of the skin surface that is to say skin exhibiting an uneven relief.

Essential oils are products obtained from starting materials of plant origin (leaves, stems, flowers or whole plant, for example).

These essential oils can be obtained according to various processes, such as steam distillation, distillation or extraction by means of volatile solvents, in particular.

According to the definition given in the international standard ISO 9235 and adopted by the Commission of the European Pharmacopoeia, an essential oil is an odorous product, generally of complex composition, obtained from a botanically defined plant starting material, either by steam distillation, or by dry distillation, or by an appropriate mechanical process without heating (cold expression). The essential oil is generally separated from the aqueous phase via a physical process which does not result in any significant change in the composition.

The choice of the technique for obtaining an essential oil depends mainly on the starting material: its original state and its characteristics, its nature per se. The "essential oil/plant starting material" yield may be extremely variable depending on the plants, 15 ppm to more than 20%. This choice conditions the characteristics of the essential oil, in particular viscosity, colour, solubility, volatility, richness or poorness in certain constituents.

Mention may be made, among the methods for obtaining an essential oil, of steam distillation, which can, for example, be carried out by dry distillation or hydrodistillation. Hydrodistillation can be carried out on a glass apparatus, such as that defined in the European Pharmacopoeia for the determination of the essential oil from a plant material.

Steam distillation corresponds to the vaporization, in the presence of steam, of a substance which is not very miscible with water. The starting material is brought together with water brought to boiling point (hydrodistillation) or with steam in a still (dry distillation). The steam entrains the essential oil vapour, which is condensed in the condenser in order to be recovered as liquid phase in a Florentine flask (or essence jar), where the essential oil is separated from the water by settling. The term "aromatic water" or "hydrolate" or "distilled floral water" is used to describe the aqueous distillate which remains after the steam distillation, once the essential oil has been separated.

Essential oils are generally volatile and liquid at ambient temperature (25° C.), which distinguishes them from said "set" oils. They are more or less coloured and their density is generally less than that of water. They have a high refractive index and most of them deflect polarized light. They are liposoluble and soluble in the usual organic solvents, can be steam distilled, and have very low solubility in water.

The plant *Origanum majorana* is a plant of the family Lamiaceae. It is an annual or perennial plant approximately 50 to 60 cm in height. This plant can in particular be found in the south of France. It is more commonly known as sweet marjoram.

According to the invention the *origanum* hybrids can be hybrids of *origanum,* in particular hybrids of *Origanum majorana,* or can be interspecific hybrids, in particular hybrids of *Origanum majorana* and another species of *Origanum.*

According to the invention, the essential oil capable of being used is an essential oil of *Origanum majorana,* and/or an essential oil of *origanum* hybrids.

Advantageously, the essential oil capable of being used according to the present invention is an essential oil of *Origanum majorana* L., in particular of *Origanum majorana* L. CT thujanol, also called *Origanum X majoricum Cambassedes.*

The essential oil of *Origanum majorana* in accordance with the invention can advantageously be obtained from the aerial part of the plant. Moreover, harvesting can be carried out at various stages of cutting: beginning of flowering or end of flowering and preferably at the end-of-flowering stage.

The chemical composition of the essential oil of *Origanum majorana* in accordance with the invention can be analaysed by conventional techniques known to those skilled in the art, such as gas chromatography GC analysis, chromatographic analysis with flame ionization detection, referred to as GC-FID, or GC/MS analysis, which consists of the use of a mass spectrometer coupled to a gas chromatograph.

The essential oil of *Origanum majorana* and/or of *origanum hybrids in accordance with the invention is characterized in that it comprises more than 18% by weight of* cis-4-thujanol and more than 16% by weight of carvacrol relative to the total weight of the constituents of the essential oil.

More particularly, the essential oil of *Origanum majorana* and/or of *origanum* hybrids in accordance with the invention is characterized in that it comprises more than 18% by weight of cis-4-thujanol and more than 18% by weight of carvacrol.

According to the invention, the cis-4-thujanol is present in the essential oil of *Origanum majorana* and/or of *origanum* hybrids in a content greater than or equal to 18% by weight, preferably greater than or equal to 20% by weight, and preferentially from 22% to 35% by weight relative to the total weight of the constituents of the essential oil.

According to the invention, the carvacrol is present in the essential oil of *Origanum majorana* and/or of *origanum* hybrids in a content greater than or equal to 16% by weight, particularly in a content greater than or equal to 18% by weight, more particularly in a content greater than or equal to 20% by weight, and more preferentially from 22% to 25% by weight.

The two major constituents which are part of the composition of the essential oil in accordance with the invention are therefore:
  cis-4-thujanol, present in a content greater than or equal to 18% by weight, preferably greater than or equal to 20% by weight, and preferentially from 22% to 35% by weight relative to the total weight of the constituents of the essential oil;
  carvacrol, present in a content greater than or equal to 16% by weight relative to the total weight of the constituents of the oil, preferably in a content greater than or equal to 18% by weight, more particularly in a content greater than or equal to 20% by weight, and more preferentially from 22% to 25% by weight.

Preferably, the following constituents are also generally present in the essential oil according to the invention in concentrations greater than 1.8% by weight relative to the total weight of the constituents, in particular ranging from 2% to 8% by weight:
  terpinen-4-ol,
  gamma-terpinene,
  para-cymene,
  sabinene,
  alpha-terpinene,
  trans-4-thujanol.

The invention also relates to a composition, in particular a cosmetic composition, comprising at least one essential oil of *Origanum majorana* and/or of *origanum* hybrids as defined above, in particular intended for treating and/or preventing greasy or greasy-prone skin and/or the associated aesthetic skin defects.

The essential oil of *Origanum majorana* and/or of *origanum* hybrids in accordance with the invention may be present in the cosmetic composition in a content of between 0.0001% and 5%, in particular in a content of between 0.001% and 5%, in particular between 0.01% and 3%, more particularly between 0.05% and 2%, even better still between 0.01% and 5%, and even better still between 0.01% and 1% by weight relative to the total weight of the composition. Preferably, the essential oil of *Origanum majorana* and/or of *origanum* hybrids in accordance with the invention may be present in the cosmetic composition in a content of between 0.01% and 1% by weight relative to the total weight of the composition.

A subject of the present invention is also the cosmetic use of at least one essential oil of *Origanum majorana* and/or of *origanum* hybrids as defined above, or of a cosmetic composition comprising same, as an agent for treating and/or preventing greasy skin or greasy-prone skin and/or the associated aesthetic skin defects.

More particularly, a subject of the invention is the cosmetic use of at least one essential oil of *Origanum majorana* L., in particular of *Origanum majorana* L. CT thujanol or of *Origanum* X *majoricum Cambassedes,* or of a cosmetic composition comprising same, as an agent for treating and/or preventing greasy skin or greasy-prone skin and/or the associated aesthetic skin defects.

Preferably, a subject of the invention is a cosmetic use as defined above, characterized in that said essential oil, or the composition comprising same, is intended for topical administration, said cosmetic composition comprising a physiologically acceptable medium.

More particularly, a subject of the invention is a cosmetic use as defined above, characterized in that the aesthetic defects are skin imperfections associated with the development of *Propionibacterium acnes* microorganisms.

More particularly, a subject of the invention is a cosmetic use as defined above, characterized in that the aesthetic skin defects are skin imperfections chosen from skin exhibiting follicular orifices or pores which are dilated, skin exhibiting follicular orifices or pores which are filled with horny spicules or with comedones and/or blackheads, a thick skin grain, and rough skin or skin exhibiting an uneven relief.

The invention also relates to a cosmetic treatment process for treating and/or preventing greasy or greasy-prone skin and/or the associated aesthetic skin defects, characterized in that it comprises the topical application of a cosmetic composition comprising, in a physiologically acceptable medium, an essential oil of *Origanum majorana* and/or of *origanum* hybrids comprising more than 18% by weight of cis-4-thujanol and more than 16% of carvacrol, in particular an essential oil of *Origanum majorana* L., in particular of *Origanum majorana* L. CT thujanol or of *Origanum* X *majoricum Cambassedes.*

More particularly, the invention relates to a cosmetic treatment process for treating and/or preventing greasy or greasy-prone skin and/or the associated aesthetic skin defects, characterized in that it comprises the topical application of a cosmetic composition comprising, in a physiologically acceptable medium, an essential oil of *Origanum majorana* and/or of *origanum* hybrids comprising more than 18% by weight of cis-4-thujanol and more than 18% by weight of carvacrol, in particular an essential oil of *Origanum majorana* L., in particular of *Origanum majorana* L. CT thujanol or of *Origanum* X *majoricum Cambassedes.*

More particularly, a subject of the invention is a cosmetic treatment process described above, characterized in that said essential of *Origanum majorana* comprises more than 18% by weight of cis-4-thujanol and more than 18% by weight of carvacrol.

More particularly, a subject of the invention is a cosmetic treatment process defined above, characterized in that the aesthetic skin defects are skin imperfections chosen from a thick skin grain, skin exhibiting follicular orifices or pores which are dilated, skin exhibiting follicular orifices or pores which are filled with horny spicules or with comedones and/or blackheads, and rough skin or skin exhibiting an uneven relief.

The application of the composition comprising said oil may optionally be followed by a step of rinsing with water.

According to another embodiment, the application is repeated, for example, 1 to 3 times daily for one day or more, preferably once or twice a day, and particularly for an extended period of at least 4 weeks, or even 4 to 15 weeks with, where appropriate, one or more periods of interruption.

According to one embodiment, the cosmetic treatment process according to the invention may comprise a single application.

A cosmetic process according to the invention is dedicated in particular to individuals with greasy or greasy-prone skin and/or associated aesthetic skin defects.

An individual to whom a cosmetic treatment process of the invention relates is naturally an individual exhibiting, or capable of exhibiting, at least one of the cosmetic care indications defined above.

A process of the invention makes it possible to treat greasy or greasy-prone skin, and in particular an aesthetic defect of the skin as defined above.

Preferably, a process according to the invention will comprise the topical application of a composition according to the invention to the skin of the face.

A subject of the invention is also a non-therapeutic cosmetic care and/or cleansing process for greasy or greasy-prone skin and/or the associated aesthetic skin defects, characterized in that it comprises the topical application, to the skin, of at least one composition as defined above comprising, in a physiologically acceptable medium, an essential oil of *Origanum majorana* as defined above.

The present invention is also directed towards an essential oil of *Origanum majorana* and/or of *origanum* hybrids, as defined above, as a dermatological agent for preventing and/or treating the skin disorders associated with the development of *Propionibacterium acnes* microorganisms.

According to another aspect, the present invention is also directed towards, said essential oil of *Origanum majorana* and/or of *origanum* hybrids, as an active agent in a dermatological composition intended for preventing and/or treating the skin disorders associated with the development of *Propionibacterium acnes* microorganisms.

More particularly, said essential oil of *Origanum majorana* and/or of *origanum* hybrids is used in a dermatological composition, in particular in a content ranging from 0.0001% to 10% by weight, more particularly from 0.001% to 5% by weight, and preferably from 0.001% to 1% by weight relative to the total weight of the dermatological composition.

A composition in accordance with the invention, namely intended for the implementation of the invention, may be a cosmetic or dermatological composition according to the application envisaged, and therefore comprises a physiologically acceptable medium.

For the purposes of the present invention, the term "physiologically acceptable medium" is intended to mean a medium suitable for the topical administration of a composition, and compatible with all the keratin materials, such as the skin, the scalp, the nails, the mucous membranes, the eyes and the hair, or any other area of bodily skin.

A physiologically acceptable medium can be a dermatologically or cosmetically acceptable medium; it is preferentially a cosmetically acceptable medium, i.e. devoid of odour or unpleasant appearance, and which is entirely compatible with the topical administration route.

In the present case, the composition is intended to be administered topically, i.e. by application at the surface of the skin under consideration.

The cosmetic or dermatological compositions capable of being used in the context of the invention generally comprise a physiologically acceptable medium, preferably a cosmetically acceptable medium.

The compositions according to the invention may be in all the galenical forms conventionally used for topical application and in particular in the form of aqueous or aqueous-alcoholic solutions, of oil-in-water (O/W), water-in-oil (W/O) or multiple (triple W/O/W or O//O) emulsions, of aqueous gels or of dispersions of a fatty phase in an aqueous phase using spherules, it being possible for these spherules to be lipid vesicles of ionic and/or non-ionic type (liposomes, niosomes or oleosomes). These compositions are prepared according to the usual methods.

The compositions according to the invention may also be in anhydrous form, for instance in the form of an oil. The term "anhydrous composition" is intended to mean a composition containing less than 1% by weight of water, or even less than 0.5% water, and in particular free of water, the water not being added during the preparation of the composition but corresponding to the residual water provided by the mixed ingredients.

Advantageously, the compositions according to the invention are in the form of a gel, or of an emulsion, of a powder or of a paste.

In addition, the composition according to the invention may be more or less fluid and may have the appearance of a white or coloured cream, an ointment, a milk, a lotion, a serum, a paste, a foaming gel, a care product, a tonic or a foam. It can optionally be applied to the skin in aerosol form. It can also be in solid form, and for example in the form of a stick.

When the composition used according to the invention comprises an oily phase, it preferably contains at least one oil. It may also contain other fatty substances.

As oils that may be used in the composition of the invention, examples that may be mentioned include:

hydrocarbon-based oils of animal origin, such as perhydrosqualene;

hydrocarbon-based oils of vegetable origin, such as liquid triglycerides of fatty acids comprising from 4 to 10 carbon atoms, such as heptanoic or octanoic acid triglycerides, or alternatively, for example, sunflower oil, maize oil, soybean oil, cucumber oil, grape seed oil, sesame seed oil, hazelnut oil, apricot oil, macadamia oil, arara oil, castor oil, avocado oil, caprylic/capric acid triglycerides, such as those sold by the company Stearineries Dubois or those sold under the names Miglyol 810, 812 and 818 by the company Dynamit Nobel, jojoba oil and shea butter oil;

synthetic esters and ethers, in particular of fatty acids, for instance the oils of formulae $R'COOR^2$ and $R'OR^2$ in which R' represents the residue of a fatty acid comprising from 8 to 29 carbon atoms, and $R^2$ represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of inorganic or synthetic origin, such as volatile or non-volatile liquid paraffins, and derivatives thereof, petroleum jelly, polydecenes, and hydrogenated polyisobutene such as Parleam oil;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils, for instance those described in document JP-A-2-295912;

silicone oils, for instance volatile or non-volatile polymethylsiloxanes (PDMS) with a linear or cyclic silicone chain, which are liquid or pasty at ambient temperature, in particular cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;

mixtures thereof.

In the list of the abovementioned oils, the term "hydrocarbon-based oil" is intended to mean any oil predominantly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin wax, beeswax, carnauba wax or candelilla wax, paraffin waxes, lignite wax or microcrystalline waxes, ceresin or ozokerite, and synthetic waxes, for instance polyethylene waxes and Fischer-Tropsch waxes; silicone resins such as trifluoromethyl-$C_1$-$C_4$-alkyl dimethicone and trifluoropropyl dimethicone; and silicone elastomers, for instance the products sold under the name KSG by the company Shin-Etsu, under the name Trefil, BY29 or EPSX by the company Dow Corning, or under the name Gransil by the company Grant Industries.

These fatty substances can be chosen in a varied manner by a person skilled in the art so as to prepare a composition having the desired properties, for example of consistency or texture.

According to one particular embodiment of the invention, the composition according to the invention is a water-in-oil (W/O) or oil-in-water (O/W) emulsion. The proportion of the oily phase of the emulsion may range from 5% to 90% by weight and preferably from 5% to 60% by weight relative to the total weight of the composition.

The emulsions generally contain at least one emulsifier chosen from amphoteric, anionic, cationic and non-ionic emulsifiers, used alone or as a mixture, and optionally a co-emulsifier. The emulsifiers are appropriately chosen according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For the W/O emulsions, examples of emulsifiers that may be mentioned include dimethicone copolyols such as the mixture of cyclomethicone and of dimethicone copolyol sold under the name DC 5225 C by the company Dow Corning, and alkyl dimethicone copolyols such as the lauryl methicone copolyol sold under the name Dow Corning 5200 Formulation Aid by the company Dow Corning and the cetyl dimethicone copolyol sold under the name Abil EM 90® by the company Goldschmidt. A crosslinked elastomeric solid organopolysiloxane comprising at least one oxyalkylene group, such as those obtained according to the procedure of Examples 3, 4 and 8 of document U.S. Pat. No. 5,412,004 and of the examples of document U.S. Pat. No. 5,811,487, in particular the product of Example 3 (synthesis example) of patent U.S. Pat. No. 5,412,004, such as the product sold under the reference KSG 21 by the company Shin-Etsu, may also be used as surfactants for W/O emulsions.

For the O/W emulsions, examples of emulsifiers that may be mentioned include non-ionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof, such as the mixture of glyceryl stearate and PEG-40 stearate.

The composition according to the invention may also contain adjuvants which are customary in the cosmetics field, such as hydrophilic or lipophilic gelling agents, preservatives, water, solvents, fragrances, fillers, waxes, pasty fatty substances, UV-screening agents, odour absorbers, colorants, basic agents, acids, or non-ionic, anionic or cationic surfactants.

The amounts of these various adjuvants are those conventionally used in the field under consideration, and are for example from 0.01% to 20% of the total weight of the composition. Depending on their nature, these adjuvants may be introduced into the fatty phase, into the aqueous phase and/or into the lipid vesicles.

The compositions according to the invention may also comprise at least one aqueous phase.

The aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

Needless to say, a person skilled in the art will take care to select this or these optional additional ingredients and/or active agents, and/or the amount thereof, such that the advantageous properties of the essential oil of sweet marjoram according to the invention are not, or are not substantially, adversely affected by the envisaged addition.

The compositions according to the invention may be applied directly to the skin or, alternatively, to cosmetic supports of occlusive or non-occlusive type, intended to be applied locally to the skin. By way of non-limiting examples of cosmetic supports, mention may in particular be made of a patch, a wipe, a roll-on and a pen.

The composition according to the present invention will comprise, according to one particular embodiment, in addition to the essential oil of sweet marjoram as defined above, at least one additional active agent for caring for greasy or greasy-prone skin.

The expression "additional active agent for caring for greasy skin" is intended to mean, in the context of the present invention, a compound which, by itself, i.e. not requiring the intervention of an external agent to activate it, has a biological activity which may in particular be:

a desquamating activity (which makes it possible to open comedones), and/or an antimicrobial activity (in particular on *P. acnes*), and/or a soothing or anti-inflammatory activity, and/or a sebum-regulating activity, and/or an antioxidant activity (which prevents squalene oxidation and comedone formation);

a healing activity;
an astringent activity.

The additional active agent for caring for greasy skin that can be used in the compositions of the invention is preferentially chosen from desquamating agents, antimicrobial agents, soothing agents, anti-inflammatory agents, sebum-regulating agents, antioxidants, healing agents, astringent agents, and mixtures thereof.

The additional active agent for caring for greasy skin that is used in the composition according to the invention can represent from 0.0001% to 20%, preferably from 0.01% to 10% and even better still from 0.01% to 5% by weight relative to the total weight of the composition.

The cosmetic composition may optionally be rinsed after having been applied to the skin. Moreover, after the application of the cosmetic composition according to the invention, a composition comprising one or more active agents chosen from antibacterial agents, antifungal agents and/or powders may be applied to the surface of the skin.

The process according to the invention may prove to be quite particularly of use:
  for preventing and/or treating the aesthetic defects of greasy or greasy-prone skin,
  for preventing and/or treating skin exhibiting follicular orifices or pores which are dilated, in particular for reducing the appearance and/or the visibility of the pores, in particular for closing the pores and/or reducing the size of the pores, and/or reducing the number of visible pores,
  for preventing and/or treating skin exhibiting follicular orifices or pores filled with horny spicules or with comedones, or skin exhibiting comedones and/or blackheads,
  for preventing and/or treating rough skin or skin exhibiting an uneven relief.

The process according to the invention may also prove to be of use for treating and/or preventing the skin defects or imperfections which are associated with the development of *Propionibacterium acnes* microorganisms.

According to one particular embodiment of the invention, other agents intended to make the appearance and/or the texture of the skin more attractive may also be added to the composition suitable for use in the invention.

Throughout the description, including the claims, the expression "comprising a" should be understood as being synonymous with "comprising at least one", unless otherwise specified.

The expressions "more than", "between . . . and . . . " and "ranging from . . . to . . . " should be understood as being limits inclusive, unless otherwise specified.

The examples and figures that follow are presented as non-limiting illustrations of the invention. The compounds are, depending on the case, cited as the chemical names or as the CTFA names (International Cosmetic Ingredient Dictionary and Handbook).

In these examples, the term "cfu" denotes "colony-forming unit". It is the unit of measurement used to quantify live bacteria.

The invention is illustrated in greater detail in the examples that follow.

EXAMPLE 1

Production of an Essential Oil of *Origanum Majorana* According to the Invention An essential oil of *Origanum majorana* was prepared by distillation of 300 g of fresh aerial part picked at the blossomed to deblossomed stage, in an apparatus of Clevenger type by dry distillation, for 1 h 30. An essential oil was obtained with a yield of about 1.05%.

The essential oil thus obtained contains:
terpinen-4-ol 9.2%
γ-terpinene 7.4%
p-cymene 2.2%
sabinene 5.3%
α-terpinene 3.8%
trans-4-thujanol 2.8%
cis-4-thujanol 25.6%
α-terpineol 2.3%
linalyl acetate 3.0%
carvacrol 20.4%

The composition of the essential oil obtained was determined by GC (gas chromatography) and mass spectrometry.

EXAMPLE 2

Effect of an Essential Oil of *Origanum Majorana* According to the Invention on the Growth of *Propionibacterium Acnes* Microorganisms Associated with Greasy Skin This test enables the quantitative determination of the bactericidal activity of an essential oil of *Origanum majorana* according to Example 1, in accordance with the invention, with respect to microorganisms under optimum growth conditions, namely microorganisms of the *Propionibacterium acnes* ATCC 6919 type originating from the Institut Pasteur and maintained according to the requirements of standard EN 12353, grown on tryptic soy agar—TSA (Difco) in an anaerobic jar for 5 days at 32.5° C.±2.5° C.

Nutritive broths containing a double concentration of the *Propionibacterium acnes* strains (approximately 2 to 6×10$^5$ CFU/ml) are prepared.

A stock solution at 10% (w/v) of an essential oil of *Origanum majorana* according to the invention is prepared in 1% agar. After stirring, dilutions are carried out in order to prepare solutions of essential oil of *Origanum majorana* at 0.02%, 0.1%, 0.2%, 1% and 2% (w/v). The nutritive broths of *P. acnes* obtained are brought into contact with the essential of *Origanum majorana* according to the invention at the various abovementioned concentrations. The test samples thus obtained are in the form of opaque emulsions containing 0.1%, 0.5% and 1% (w/v) of essential oil.

After incubation for 24 hours at 32.5° C.±2.5° C., the surviving microorganisms are counted by spiral inoculation and compared with the initial inoculum in order to define the reduction levels obtained. A value of 5 log is assigned to the initial inoculum.

Spiral inoculation systems use a semi-automatic inoculator which deposits a calibrated volume of a liquid sample at the surface of an agar placed on a rotating plate, while describing an Archimedean spiral. After incubation, reading is carried out using graphs. This technique makes it possible to carry out the bacterial count of a sample on one and the same dish, dispensing with all or some of the intermediate dilutions. This methodology is much used and is an officially accepted technique.

By means of a method of dilution in liquid medium, various concentrations of product are brought into contact with a nutritive broth inoculated with the test strain. After incubation, the surviving microorganisms are counted (log).

The concentrations of essential oil of *Origanum majorana* according to the invention in terms of product tested are:

0.01%, 0.05%, 0.1%, 0.5% and 1% (v/v or w/v). The diluent used is 1% agar. The appearance in the broth is an opaque emulsion.

The results are recapitulated in the table hereinafter.

|  | Initial inoculum/After 24 hours of contact time | | | | |
|---|---|---|---|---|---|
| Essential oil of *Origanum majorana* according to Example 1 | Concentration of essential oil (w/v): 0.01% | 0.05% | 0.1% | 0.5% | 1% |
| *Propionibacterium acnes* (log) | 5.5 | 2.5 | 0 | 0 | 0 |

The results indicate that, after having inoculated 5.2 log into the medium containing various concentrations of essential oil, the decontamination is about 2.7 log of the bacterial population after 24 h, from 0.05% (w/v), and there is a total decontamination of the microbial population starting from 0.1%.

Thus, the essential oil of *Origanum majorana* in accordance with the invention makes it possible to reduce the growth of *P. acnes* microorganisms and, consequently, to prevent and/or treat the skin disorders and/or the skin imperfections associated with the development of these microorganisms.

EXAMPLE 3

Effect of an Essential Oil of *Origanum Majorana* According to the Invention on the Cohesion of the Stratum Corneum of Viable Excised Skin Fragments of normal human skin, or explants, were obtained by plastic surgery (6 different donors). They were placed in inserts, comprising a porous membrane (8 μm), themselves placed on culture wells containing a culture medium as described in Boisnic et al., (Journal of Cosmetics and laser therapy, 2010:12:25-31).

The protocol consisted in applying the following treatments topically to the skin explants: absence of treatment (untreated control); squalane solution (placebo); essential oil of *Origanum majorana* in accordance with the invention, applied at 0.5% in squalane.

The concentration indicated corresponds to the final concentration applied to the surface of the skin.

The semi-quantitative scores of the cohesion of the stratum corneum are determined from histological sections stained with hemalun-eosin. The morphology of the stratum corneum (SC) is analysed 2 days later on a biopsy.
Score 0: absence of modification of the cohesion of the stratum
Score 1: slight decrease in cohesion
Score 2: moderate decrease
Score 3: large decrease
Score 4: very large decrease The study made it possible to evaluate the influence of an essential oil of *Origanum majorana* according to the invention, at a concentration of 0.5% in solution in squalane, on the cohesion of the stratum corneum (SC) of a human skin explant maintained under survival conditions.

The average score of the cohesion of the SC after treatment with an essential oil of *Origanum majorana* according to the invention at 0.5% is 2.42. This increase in the score compared with squalane and the placebo (average score of 1.76) and compared with the control skin (average score of 1.38) is statistically significant (student's test $p<0.05$).

The results show that the application of an essential oil of *Origanum majorana* according to the invention, at 0.5%, limits the cohesion of the stratum corneum of the skin explant. The higher the score, the weaker the cohesion of the stratum corneum.

The essential oil of *Origanum majorana*, at 0.5% in squalane, significantly modifies the cohesion of the SC compared with the SC of control skin, or with the placebo (squalane).

This result demonstrates the desquamating effect on the skin of an essential oil of *Origanum majorana* according to the invention, and also its properties with regard to the surface condition of the skin, to a condition associated with greasy skin, such as, in particular, skin imperfections chosen from a thick skin grain, rough skin or skin exhibiting an uneven relief.

EXAMPLE 4

Composition According to the Invention for Caring for Greasy Skin

The amounts are given as weight percentages relative to the total weight of the composition.

| | |
|---|---|
| Xanthan gum (RHODICARE XC ® sold by the company Rhodia) | 0.2% |
| Ethylenediaminetetraacetic acid | 0.05% |
| Trisodium citrate | 0.05% |
| Cetyl alcohol | 0.25% |
| Polydiméthylsiloxane (Viscosity: 100 CST) | 0.5% |
| Cyclohexadimethylsiloxane (Viscosity: 8 CST) | 6% |
| Glyceryl stearate (and) PEG-100 stearate (Arlacel ® 165 sold by the company CRODA) | 0.15% |
| Polyacrylamidomethylpropanesulfonic acid partially neutralized with aqueous ammonia and highly crosslinked (Hostacerin ® AMPS sold by the company Clariant) | 2% |
| Sodium hydroxide | 0.3% |
| Essential oil of *Origanum majorana* according to Example 1 | 0.5% |
| Fragrance | 0.5% |
| Ethyl alcohol | 5% |
| Glycerol | 5% |
| Hydrogenated isoparaffin | 2% |
| Water q.s. | 100% |

This composition, applied to the skin, makes it possible to treat and/or prevent greasy or greasy-prone skin and/or the associated aesthetic skin defects such as the skin imperfections described in the present application.

The invention claimed is:

1. A cosmetic treatment process for treating greasy or greasy-prone skin, which comprises the topical application, to the greasy or greasy-prone skin, of at least one composition comprising, in a physiologically acceptable medium, at least 0.05% by weight of the composition of an essential oil of *Origanum majorana* or hybrid of *Origanum majorana*, or hybrid of *Origanum majorana* and another species of *Origanum*, or mixture thereof; said essential oil comprising 22 to 35% by weight of cis-4-thujanol and 22 to 25% by weight of carvacrol and 2 to 8% by weight of at least one of the following:
    terpinen-4-ol,
    gamma-terpinene,
    para-cymene,
    sabinene,
    alpha-terpinene,
    trans-4-thujanol relative to the total weight of the constituents of the essential oil.

2. The cosmetic process according to claim 1, wherein development of *Propionibacterium acnes* microorganisms is associated with the greasy or greasy-prone skin.

3. The cosmetic process according to claim 1, wherein aesthetic skin defects are associated with the greasy or greasy-prone skin and are chosen from a thick skin grain, skin exhibiting follicular orifices or pores which are dilated, skin exhibiting follicular orifices or pores which are filled with horny spicules or with comedones and/or blackheads, and rough skin or skin exhibiting an uneven relief.

4. A non-therapeutic cosmetic care and/or cleansing process for greasy or greasy-prone skin, which comprises the topical application, to the greasy or greasy-prone skin, of at least one composition comprising, in a physiologically acceptable medium, at least 0.05% by weight of the composition of an essential oil of *Origanum majorana* or hybrid of *Origanum majorana*, or hybrid of *Origanum majorana* and another species of *Origanum*, or mixture thereof; said essential oil, comprising 22 to 35% by weight of cis-4-thujanol and 22 to 25% by weight of carvacrol and 2 to 8% by weight of at least one of the following:
  terpinen-4-ol,
  gamma-terpinene,
  para-cymene,
  sabinene,
  alpha-terpinene,
  trans-4-thujanol
relative to the total weight of the constituents of the essential oil.

5. The cosmetic process according to claim 1, wherein said essential oil is an essential oil of *Origanum majorana* L.

6. The cosmetic process according to claim 1, wherein said essential oil of is an essential oil of *Origanum majorana* L. CT thujanol or of *Origanum X majoricum Cambassedes*.

7. The cosmetic process according to claim 1, wherein said essential oil of *Origanum majorana* or hybrid of *Origanum majorana*, or hybrid of *Origanum majorana* and another species of *Origanum*, or mixture thereof, is present in the composition in a content of up to 5% by weight relative to the total weight of the composition.

8. The cosmetic process according to claim 1, wherein said essential oil of *Origanum majorana* or hybrid of *Origanum majorana*, or hybrid of *Origanum majorana* and another species of *Origanum*, or mixture thereof, is present in the composition in a content of up to 3% by weight relative to the total weight of the composition.

9. The cosmetic process according to claim 1, wherein said essential oil of *Origanum majorana* and/or *origanum* hybrids, is present in the composition in a content of 0.05% to 2% by weight relative to the total weight of the composition.

10. The cosmetic process according to claim 1, wherein said essential oil of *Origanum majorana* or hybrid of *Origanum majorana*, or hybrid of *Origanum majorana* and another species of *Origanum*, or mixture thereof, is present in the composition in a content of up to 1% by weight relative to the total weight of the composition.

* * * * *